(12) United States Patent
Grant et al.

(10) Patent No.: US 12,156,643 B2
(45) Date of Patent: Dec. 3, 2024

(54) ADJUSTABLE VASCULAR CLOSURE DEVICE

(71) Applicant: Vivasure Medical Limited, Galway (IE)

(72) Inventors: Peter Grant, Galway (IE); Mark McGoldrick, Athlone (IE); Gerard Brett, Claregalway (IE); Christopher Martin, Oughterard (IE)

(73) Assignee: Vivasure Medical Limited, Galway (IE)

( * ) Notice: Subject to any disclaimer, the term of this patent is extended or adjusted under 35 U.S.C. 154(b) by 617 days.

(21) Appl. No.: 17/311,192

(22) PCT Filed: Dec. 20, 2019

(86) PCT No.: PCT/EP2019/086846
§ 371 (c)(1),
(2) Date: Jun. 4, 2021

(87) PCT Pub. No.: WO2020/141122
PCT Pub. Date: Jul. 9, 2020

(65) Prior Publication Data
US 2022/0031294 A1   Feb. 3, 2022

Related U.S. Application Data

(60) Provisional application No. 62/786,789, filed on Dec. 31, 2018.

(51) Int. Cl.
*A61B 17/00* (2006.01)
(52) U.S. Cl.
CPC ............... *A61B 17/0057* (2013.01); *A61B 2017/00477* (2013.01); *A61B 2017/00575* (2013.01);
(Continued)

(58) Field of Classification Search
CPC ...... A61B 2017/00672; A61B 17/0057; A61B 2017/00575; A61B 2017/00588;
(Continued)

(56) References Cited

U.S. PATENT DOCUMENTS

| 4,368,736 A | * | 1/1983 | Kaster | ............ A61F 2/064 606/153 |
| 5,350,399 A | * | 9/1994 | Erlebacher | ......... A61B 17/0057 606/151 |

(Continued)

FOREIGN PATENT DOCUMENTS

| CN | 101028205 A | 9/2007 |
| CN | 103391750 A | 11/2013 |

(Continued)

OTHER PUBLICATIONS

International Search Report for PCT/EP2019/086846, mailed Mar. 12, 2020, 5 pages.
(Continued)

*Primary Examiner* — Brooke Labranche
*Assistant Examiner* — Mitchell Brian Hoag
(74) *Attorney, Agent, or Firm* — Choate, Hall & Stewart LLP; William R. Haulbrook; Peter A. Flynn (57) ABSTRACT

The disclosed technology provides a device (10) for sealing an aperture in a tissue of a body lumen. The device includes a flexible support member (14) having a base (19) configured to engage and/or hold a sealable member (12) of the device against an interior surface of the tissue when the device is in the sealing position. The device also includes a locator (16) coupled to the support member and configured to engage with a wall of the body lumen to secure the device thereto.

18 Claims, 9 Drawing Sheets

(52) U.S. Cl.
CPC ............... *A61B 2017/00588* (2013.01); *A61B 2017/00606* (2013.01); *A61B 2017/00615* (2013.01); *A61B 2017/00623* (2013.01); *A61B 2017/00659* (2013.01); *A61B 2017/00672* (2013.01)

(58) Field of Classification Search
CPC ........... A61B 2017/00592; A61B 2017/00637; A61B 2017/00641; A61B 2017/1205; A61B 17/12022; A61B 17/12113; A61B 2017/12054; A61B 17/12109; A61F 2/0063
See application file for complete search history.

(56) References Cited

U.S. PATENT DOCUMENTS

| | | | |
|---|---|---|---|
| 6,533,749 B1 | 3/2003 | Mitusina et al. | |
| 7,407,078 B2 | 8/2008 | Shelton, IV et al. | |
| 8,361,092 B1* | 1/2013 | Asfora | A61B 17/08 623/1.23 |
| 2001/0041902 A1* | 11/2001 | Lepulu | A61F 2/94 606/153 |
| 2003/0023267 A1 | 1/2003 | Ginn | |
| 2005/0070957 A1* | 3/2005 | Das | A61B 17/0057 606/213 |
| 2005/0192604 A1* | 9/2005 | Carson | A61F 2/2493 606/153 |
| 2005/0273135 A1* | 12/2005 | Chanduszko | A61B 17/0057 606/213 |
| 2006/0106418 A1* | 5/2006 | Seibold | A61B 17/0057 606/213 |
| 2007/0123934 A1* | 5/2007 | Whisenant | A61B 17/0057 606/213 |
| 2010/0069930 A1* | 3/2010 | Roslin | A61B 17/0057 606/151 |
| 2010/0234878 A1* | 9/2010 | Hruska | A61B 17/0057 606/213 |
| 2011/0082495 A1* | 4/2011 | Ruiz | A61B 17/0057 606/213 |
| 2011/0196420 A1* | 8/2011 | Ebner | A61M 1/915 606/213 |
| 2012/0080334 A1 | 4/2012 | Shelton, IV et al. | |
| 2013/0274795 A1* | 10/2013 | Grant | A61B 17/0057 606/213 |
| 2013/0282057 A1 | 10/2013 | Green et al. | |
| 2014/0018846 A1 | 1/2014 | Grant et al. | |
| 2014/0018847 A1* | 1/2014 | Grant | A61B 50/30 606/213 |
| 2014/0180314 A1 | 6/2014 | Asfora | |
| 2016/0095648 A1 | 4/2016 | Churchill et al. | |
| 2016/0143639 A1* | 5/2016 | Asfora | A61B 17/04 606/153 |
| 2016/0166241 A1 | 6/2016 | McGoldrick et al. | |
| 2016/0174953 A1 | 6/2016 | Grant et al. | |
| 2017/0143343 A9* | 5/2017 | Asfora | A61B 17/11 |
| 2017/0333014 A1 | 11/2017 | Grant et al. | |
| 2019/0021710 A1* | 1/2019 | McGoldrick | A61B 17/0057 |

FOREIGN PATENT DOCUMENTS

| | | | | |
|---|---|---|---|---|
| CN | 105431097 A | | 3/2016 | |
| EP | 2548518 A1 | | 1/2013 | |
| WO | WO-2001/17440 A1 | | 3/2001 | |
| WO | WO-2015/017551 A2 | | 2/2015 | |
| WO | WO-2017102941 A1 | * | 6/2017 | ......... A61B 17/0057 |
| WO | WO-2020/141122 A1 | | 7/2020 | |

OTHER PUBLICATIONS

Written Opinion for PCT/EP2019/086846, mailed Mar. 12, 2020, 8 pages.

* cited by examiner

ADJUSTABLE VASCULAR CLOSURE DEVICE

CROSS-REFERENCE TO RELATED APPLICATIONS

This application is a 371 National Phase Entry of International Application No. PCT/EP2019/086846, filed Dec. 20, 2019, which claims priority to and the benefit of U.S. Provisional Application No. 62/786,789, filed Dec. 31, 2018. The entire contents of each of the above-referenced applications are hereby incorporated by reference.

TECHNICAL FIELD

This application relates generally to closure systems, devices, and related methods for use in surgical procedures.

BACKGROUND

During a surgical or endoscopic operation on a body lumen, e.g., a blood vessel, an aperture is formed (e.g., from an arteriotomy) in the tissue of the lumen. Following the procedure, the aperture has to be closed in order for the lumen to heal. One relatively new type of closure apparatus has a flexible disc that is delivered into the body lumen to seal the aperture. The disc maintains the tissue in apposition until the lumen is healed, allowing the wound to heal from the inside of the lumen. The disc may operate in conjunction with a rigid core, which prevents the disc from dislodging from the sealing position.

In certain patient groups, the area surrounding the tissue within the body lumen is diseased and/or has accumulation (e.g., plaque or calcified lesions on the tissue wall). Due to the irregular surface topology of such areas, the effectiveness of the seal made by certain closure apparatuses is reduced, as channels are formed between the disc and the tissue surface.

There are benefits of improving the seal formed by a closure apparatus when closing an aperture formed in the tissue of the body lumen.

SUMMARY

Generally, this disclosure relates to an implant closure device having a flexible sealable member and a flexible support member that operate in conjunction to improve a seal formed between the sealable member and the tissue surface of the body lumen during closure of an aperture in the body lumen. The support member pushes the peripheral portions of the sealable member against an interior tissue of the body lumen and provides greater rigidity to the peripheral regions of the flexible sealable member. The structure, in combination with a locator and the hydraulic pressure present in the body lumen (e.g., hemodynamic pressure of blood in a blood vessel), improves the tamponade formed by the device over the aperture. The structure is sufficiently flexible to bend so as to fit through the aperture during the deployment of the closure device in the body lumen.

The disclosed technologies prevent the inadvertent dislodgment of the closure device from the sealing position and reduce the risk of inadvertent pull-out of the implant device from within the lumen, e.g., during the deployment of the device or post-implantation of the device. A surgeon can assert greater force on the tissue, giving the surgeon a better tactile feedback of the positioning of the implant. As demonstrated herein, the provided technologies achieve unprecedented acute sealing time in closing a blood vessel and unprecedented loss of fluid from such vessel. In certain embodiments, the increased rigidity is directional to allow greater force to be directed to a specific area of the tissue surrounding the formed aperture.

A remarkable feature of the provided technologies is that they enable new types of interventional, surgical, and endoscopic procedures in providing a reliable and consistent closure of an aperture in a body lumen without regard to the tissue surface topography or wall thickness due to the adjustability of the locator device.

In one aspect, the invention relates to a device for sealing an aperture in a tissue of a body lumen. The device includes a sealable member positionable against an interior surface of the tissue adjacent the aperture in the tissue when the device is in a sealing position, a support member having a base and a column, where the base of the support member has a support surface to support the sealable member against the interior surface of the tissue when the device is in the sealing position and the column extends through the sealing member and the aperture and has an engagement mechanism, and a locator pivotably coupled to the support member via the engagement mechanism. The locator is positionable against an exterior surface of the tissue adjacent the aperture when the device is in the sealing position, so that at least a portion of the tissue is disposed between the locator and the sealable member. The locator includes an adjustment mechanism for accommodating varying tissue topographies, such as surface irregularities and body lumens having walls of different thicknesses.

In another aspect, the invention relates to a closure system for sealing an aperture in a tissue of a body lumen. The system includes a delivery device and a closure device. The closure device includes a sealable member positionable against an interior surface of the tissue adjacent the aperture in the tissue when the device is in a sealing position, a support member having a base and a column, where the base of the support member has a support surface to support the sealable member against the interior surface of the tissue when the device is in the sealing position and the column extends through the sealing member and the aperture and has an engagement mechanism, and a locator pivotably coupled to the support member via the engagement mechanism. The locator is positionable against an exterior surface of the tissue adjacent the aperture when the device is in the sealing position, so that at least a portion of the tissue is disposed between the locator and the sealable member. The locator includes an adjustment mechanism for accommodating varying tissue topographies as disclosed herein. The delivery device includes an attachment mechanism to releasably attach the closure device to the delivery device for delivering the closure device to the aperture in the tissue. The delivery device is also configured to deploy the closure device within the lumen, which includes expanding and positioning the sealing member within the lumen and actuating the locator.

In another aspect, the invention relates to a method of securing a device for sealing an aperture in a tissue of a body lumen. The method includes the steps of positioning at least a portion of the device within the body lumen via a delivery device, deploying a sealable member against an interior surface of the tissue adjacent the aperture in the tissue, deploying a support member having a base and a column, where the base of the support member has a support surface to support the sealable member against the interior surface of the tissue when the device is in the sealing position and the column extends through the sealing member and the aperture and comprises an engagement mechanism, and actuating a locator pivotably coupled to the support member via the engagement mechanism from a first position to a second position to engage a wall of the body lumen and secure the device in place. In some embodiments, various steps may be carried out simultaneously (e.g., the deploying of the sealable and support members), while in other situations (e.g., where the device is deployed in a vessel without a flowing liquid) the deploying steps are separate, distinct steps. In various embodiments, the method includes the step of positioning the locator relative to the column of the support member so that an adjustment mechanism on the locator engages at least a portion of the column to accommodate a lumen wall with an irregular topography as disclosed herein. In various embodiments, the adjustment mechanism engages a portion of the column so as to form an interference fit there between.

In various embodiments of the foregoing aspects, the aperture is a surgical perforation in a body cavity, such as a gastrointestinal tract, heart, peritoneal cavity, esophagus, vagina, rectum, trachea, bronchi, or a blood vessel, such as, for example, the femoral vein, the vena cava, the jugular vein, the femoral artery, the subclavian artery, the ascending aorta, and the auxiliary and brachial arteries. The device can be positioned and deployed within the lumen via a deployment tool or device, such as one including several tubular bodies slidably disposed on a cannula or similar device. In some cases, the device is configured to be deployed over a guidewire.

In additional embodiments of the foregoing aspects, the engagement mechanism includes a portion of the column that extends transversely from the top of the support surface and defining an aperture therein and a support shaft configured to be disposed within the column aperture to secure the locator to the support member, wherein the support shaft engages with a surface of the locator to provide a sealing force to the tissue. Additional engagement mechanisms are contemplated and considered within the scope of the invention, so long as they allow the locator to pivot or rotate relative to the support mechanism. Generally, the locator will also slide relative to the column as it is being pivoted into a sealing position.

In various embodiments, the locator has an elongate, substantially planar body, a non-planar distal portion (e.g., angled or arcuate), and a guide mechanism for engaging with a delivery device for deploying the locator. The adjustment mechanism is disposed along the elongate body of the locator. In some embodiments, the elongate body defines a substantially centrally located, elongate opening configured for engaging with the engagement mechanism and in some cases may form part of the adjustment mechanism.

Generally, the adjustment mechanism is formed as part of the elongate body and includes at least one of a section of the elongate body having a length of varying thickness to create a ramp for slidably engaging the engagement mechanism or a section of the elongate body includes a non-planar portion configured to flex when engaged with the engagement mechanism. The non-planar portion can include an arcuate portion of varying radii, a combination of angular portions, or both. Additionally or alternatively, the elongate body includes a cut-out portion on a top surface thereof for locking the locator in place when engaged with the engagement mechanism. In various embodiments, the guide mechanism includes two rails that are disposed at the exterior sides of the elongate body and extend upwardly from a top surface of the elongate body. The rails will define a space there between for slidably engaging the delivery device. In some embodiments, the guide mechanism could include a sleeve or similar structure. The locator can be deployed via a push-tube located on the delivery device pushing against the guide mechanism.

In various embodiments, the non-planar distal end of the elongate body can include any combination of angular and arcuate portions. For example, in one embodiment, the non-planar distal portion includes at least one angular portion. In another embodiment, the non-planar distal portion includes a first angular portion extending upwardly from the elongate body and a second angular portion extending from the first angular portion, as described in greater detail below. Generally, the non-planar distal end prevents the locator from engaging the aperture, while the second angular portion assists in pivotably deploying the locator against the tissue. In other embodiments, the non-planar distal ends include at least one curved or arcuate portions.

Referring back to the support member, in various embodiments, the column of the base of the support member includes a shoulder portion to secure the sealable member to the support member via crimping. In some embodiments, the sealing member is secured to the support member, at least until the device has substantially resorbed. In some embodiments, the sealing member is secured sufficiently to at least align and position the sealing member within the lumen. Additionally, the sealable member and the support member, collectively, form a single integrated structure. The sealable member and the support member are separate and distinct components that are mated together in a non-fixed manner.

For example, the sealing member and support member can be formed as a single piece or by permanently coupling the two components together.

In some embodiments, the column of the support member includes a substantially cylindrical base portion disposed transversely to the support surface and a neck portion extending angularly from a top portion of the base portion and defining an aperture along an axis corresponding to a longitudinal axis of a delivery device. The delivery device can be releasably attached to the closure device, for example, via a suture or braided wire that passes through the delivery device and the aperture in the neck portion. In some embodiments, neck portion forms an angle relative to the column of about 10 to 70 degrees and may have flat side surfaces for engaging with the delivery device in a fixed position. Additionally, the column can also include a shoulder configured for at least one of aligning or securing the sealable member thereto.

In various embodiments, the base of the support member includes a substantially circular scaffolding made up of one or more rings and an elongate, central spine comprising a proximal end and a distal end. The spine extends through a center point of the circular scaffolding and each of the proximal and distal ends extend beyond an outer diameter of the scaffolding. In some embodiments, the one or more rings are oriented concentrically. The central spine can be substantially rigid with at least one end thereof configured to engage with the aperture in the tissue. In various embodiments, the support member and/or the sealable member can be made of one or more of the following materials: polydioxanone, poly-L-lactide, poly-D-lactide, poly-DL-lactide, polyglycolide, ε-caprolactone, polyethylene glycol, or a co-polymer thereof. In some embodiments, the monomers that form the polymeric materials are bioabsorbable.

These and other objects, along with advantages and features of the disclosed systems and methods, will become apparent through reference to the following description and the accompanying drawings. Furthermore, it is to be understood that the features of the various embodiments described are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the disclosed systems and methods and are not intended as limiting. For purposes of clarity, not every component may be labeled in every drawing. In the following description, various embodiments are described with reference to the following drawings, in which.

DETAILED DESCRIPTION

As described herein, illustrative embodiments provide surgical closure systems, devices, and methods useful for (i) bringing about alignment of the tissues surrounding a perforation in a body lumen, thereby closing the aperture in the body lumen, (ii) forming a tamponade at the aperture when bringing about the alignment of the tissues, and (iii) maintaining the tissues surrounding the perforation in alignment until the perforation is sealed. The devices, systems, and methods are used, in some embodiments, to close a surgical perforation in a body cavity, such as the gastrointestinal tract, heart, peritoneal cavity, esophagus, vagina, rectum, trachea, bronchi, and blood vessel, including for example, but not limited to the femoral vein, the jugular vein, the vena cava, the femoral artery, subclavian artery, ascending aorta, and auxiliary and brachial arteries.

Figure 1A:
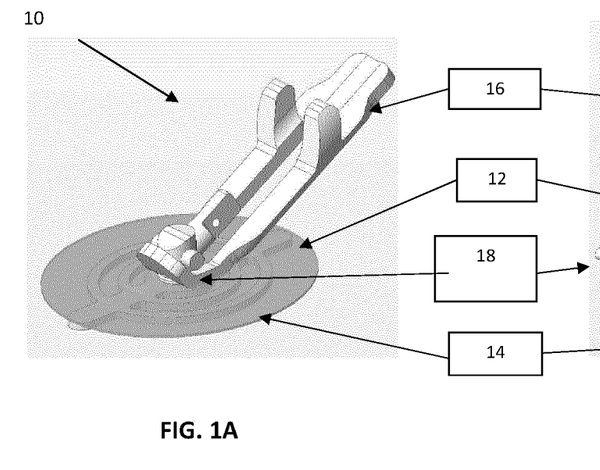
FIG. 1A is a perspective view of a fully assembled device for sealing an aperture in a tissue of a body lumen in accordance with one or more embodiments of the invention.
Figure 1B:
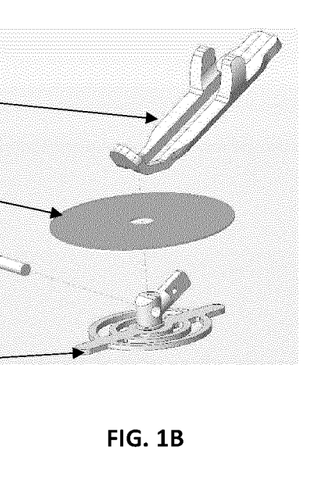
FIG. 1B is an exploded view of the device of FIG. 1A depicting the various components thereof in accordance with one or more embodiments of the invention.

FIGS. 1A and 1B depict a vascular closure implant (device 10) for closing punctures in hollow vessels. The device 10 includes four components, a flexible sealable member 12 (e.g., a patch), a support member 14 (e.g., a rigid scaffold), an extravascular supporting member (locator 16), and a locking member 18 for the extravascular supporting member (e.g., support shaft). The device 10 is shown in the assembled state in FIG. 1A, while FIG. 1B depicts the device 10 in an exploded view to illustrate each component.

Figure 2A:
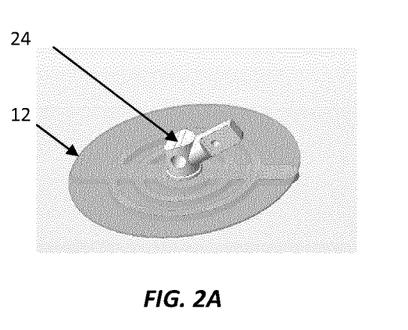
FIGS. 2A-2C are perspective views of the device of FIG. 1A in various stages of assembly in accordance with one or more embodiments of the invention.
Figure 2B:
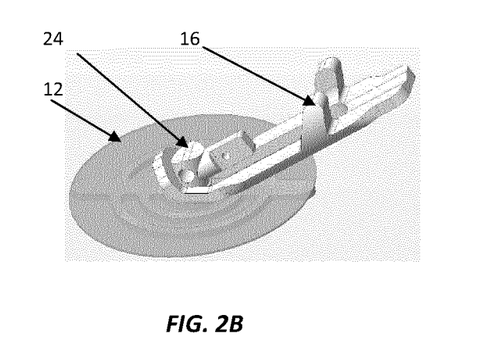
Figure 2C:
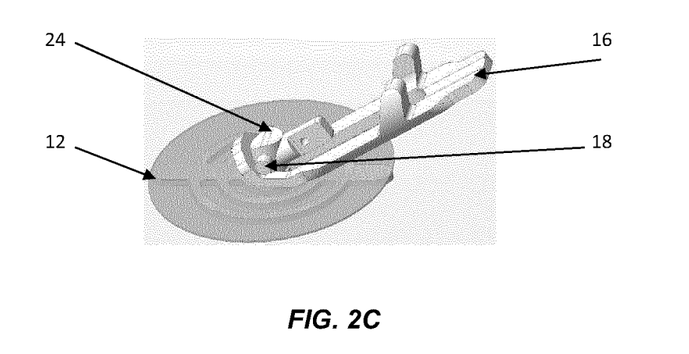

FIGS. 2A-2C depict one manner of assembling the basic closure device 10; however, other manners of assembling and different orders of steps are contemplated and considered within the scope of the invention as necessary to suit a particular application (e.g., type of the lumen, size of the lumen, and the location of the lumen). For example, in one embodiment, the device 10 is assembled by first loading the sealable member 12 on to the support member 14 (FIG. 2A). The locator 16 is then placed above the sealable member 12 (FIG. 2B). The support shaft 18 is placed through a hole in the column 24 of the support member 14 above the locator 16 (FIG. 2C), where each end the support shaft extends beyond the column 24 to secure the locator 16 to the support member 14.

Figure 21A:
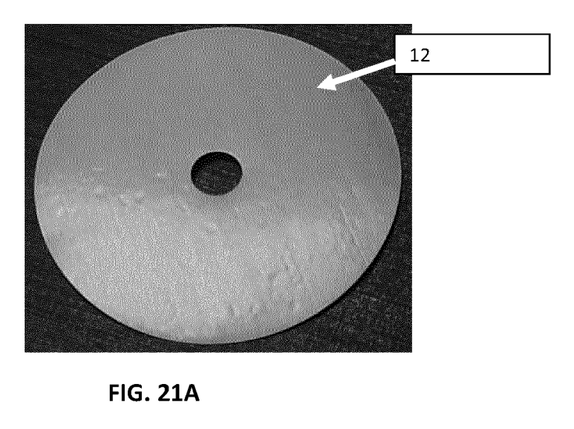
FIGS. 21A-21C are plan views of a sealing member in accordance with one or more embodiments of the invention.
Figure 21B:
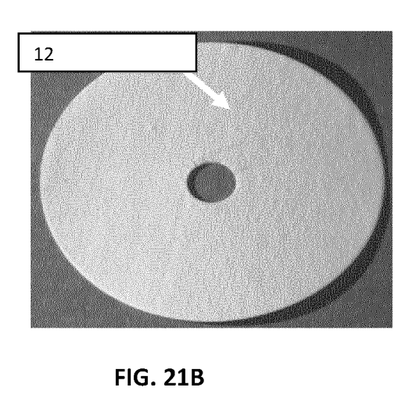
Figure 21C:
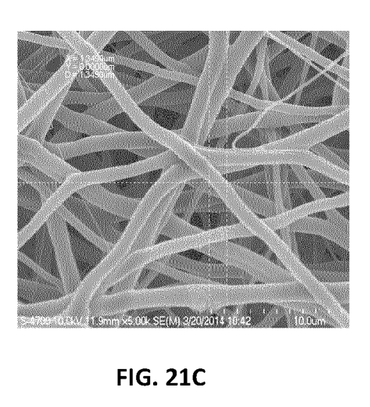

The sealable member 12 (in some embodiments this component is a flexible wing) is positionable against an interior surface of a vessel wall (e.g., 146 in FIG. 6) adjacent the aperture (e.g., 144 in FIG. 6) so as to form a tamponade at the aperture. The sealable member 12 is typically larger than a diameter of the aperture. The sealable member 12 shown has a substantially circular shape; however, other geometries (e.g., oval or polygonal) are contemplated as necessary to suit a particular application. Although flat or slightly curved when in a relaxed state, the sealable member 12 flexibly curves to conform to the interior surface of the lumen to which it engages, in the deployed state. Generally, the sealable member 12 includes an opening located at or near the center of the member 12 that is sized to pass the member 12 over the column 24. In some embodiments, the sealable member 12 is free to rotate relative to the base 19 of the support member 14 about an axis concentric to the column 24. Additional details of sealing members are disclosed in Applicant's U.S. Pat. No. 9,572,558, U.S. Patent Publication Nos. 2016/0174953 and 2017/0181736, and PCT Publication No. WO2011/080588, the entire disclosures of which are hereby incorporated by reference herein. Examples of sealable members as described in the incorporated references are shown in FIGS. 21A-21C.

Figure 3:
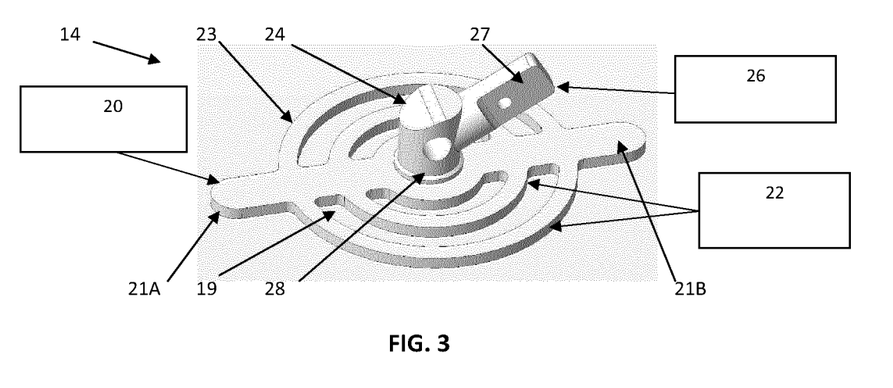
FIG. 3 is a perspective view of support member for use with the device of FIG. 1A in accordance with one or more embodiments of the invention.
Figure 4:
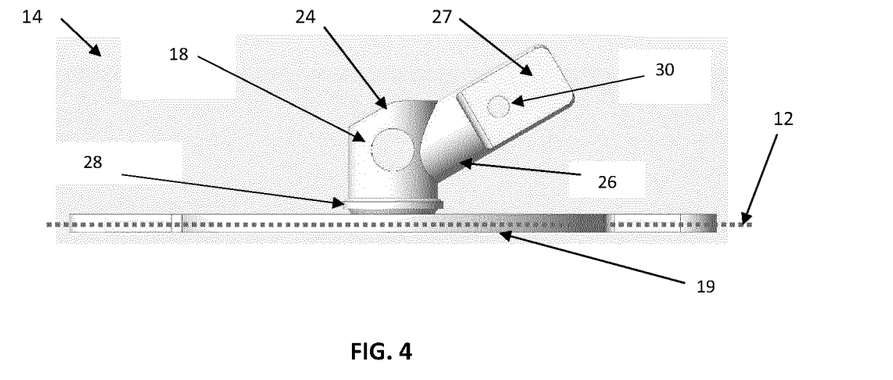
FIG. 4 is a side view of the support member of FIG. 3 in accordance with one or more embodiments of the invention.

FIGS. 3 and 4 depict the support member 14 in greater detail. As shown in FIG. 3, the support member 14 includes a base portion 19 and a column portion 24 that extends upwardly from the base 24 and substantially perpendicular thereto. In the embodiment shown, the column includes a substantially cylindrical base portion 25 and a neck portion 26 extending angularly from a top portion of the base portion 25. The neck 26 defines an aperture along an axis corresponding to a longitudinal axis of a delivery shaft to which the support member can be releasably attached. In some embodiments, the neck 26 is disposed at an angle relative to the column of about 10 to 70 degrees. The neck 26 may also include a section thereof having flat side surfaces 27 for engaging with the delivery device in a fixed position (e.g., keyed together). In some embodiments, the column further includes a shoulder 28 that can be used for at least one of aligning or securing the sealable member via, for example, crimping. In some embodiments, at least a portion of the shoulder is threaded to minimize stress and distortion on the sealable member. As shown in the figures, the column includes two apertures; one for receiving the support shaft 18 and the second in the neck 26 for receiving a suture or braided wire (e.g., 134 in FIG. 5) that is looped therethrough to allow the device 10 to be connected to a device delivery (e.g., 136 in FIG. 6).

The base 19 of the support member 14 includes a substantially circular scaffolding made up of one or more rings 22 and an elongate, central spine 20 that has a proximal end 21A and a distal end 21B. The circular scaffold shown in FIG. 3 includes two, substantially concentrically disposed rings 22 to help position and maintain the sealable member 12 in contact with the vessel luminal surface. However, other numbers of rings can be included to suit a particular application (e.g., extra-large apertures) and the rings may have other shapes and orientations (e.g., eccentric) to suit a particular application.

The spine 20 extends through a center point of the circular scaffolding and each of the proximal and distal ends 21 extend beyond an outer diameter 23 of the scaffolding. Typically, the spine 20 has a substantially rigid body, or at least a portion of the spine 20 is rigid (e.g., a central region that overlaps with the sealable member 12). At least one end 21 of the spine 20 is configured to "hook" or otherwise engage the vessel wall 46 during as the device is being pulled back to the aperture 44 in the vessel. For example, one end 21 of the spine can include a substantially planar extended portion that engages with the distal edge of the aperture, providing a tactile feeling to the user. In some embodiments, the end 21 of the spine may be reinforced (e.g., a slight thickening of the spine) to provide additional rigidity. In other embodiments, the ends 21 of the spine may include a textured surface, a widened end, or other structure to suit a particular application.

Generally the support member 14 supports the sealable member 12 during the delivery and deployment of the sealable member 12 in the body lumen by retaining and/or holding the sealable member 12 against the interior surface of the tissue when the closure device 10 is in the sealing position. The sealable member 12 and the support member 14 are depicted in a relaxed state throughout the figures; however, the members 12, 14 may be compressed, rolled, folded, or otherwise reduce in size to enable the device to be delivered to the lumen via a tubular device. Additional embodiments of support members 14 (along with exemplary dimensions for the various components) and methods for delivering and deploying the device are described in the references incorporated hereinabove.

Figure 5:
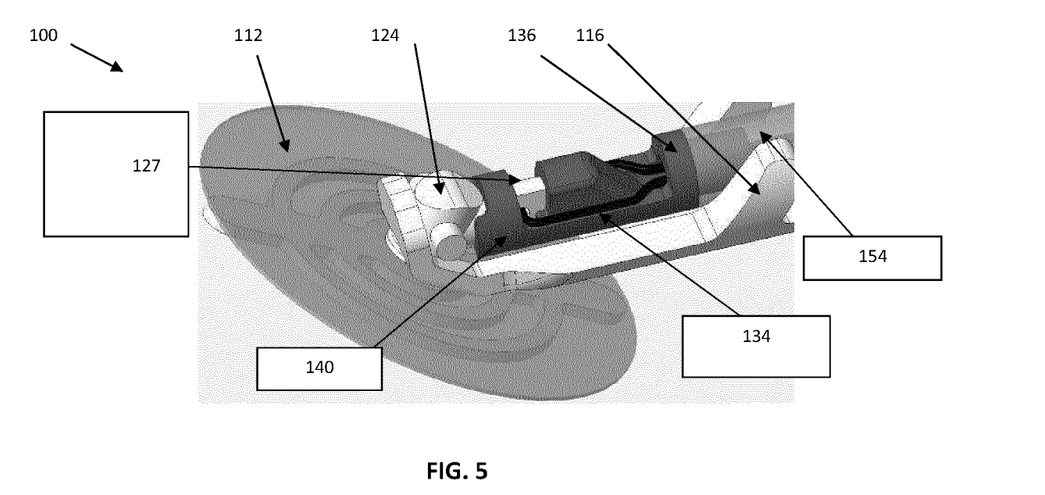
FIG. 5 is a perspective view of a fully assembled device for sealing an aperture in a tissue of a body lumen including a portion of a delivery device in accordance with one or more embodiments of the invention.

FIGS. 5-8 depict a device 100 in accordance with one or more embodiments of the invention in various states of deployment. In FIG. 5, the device 100 is shown fully assembled and loaded on the front of a delivery device 136, where the tubular body of the delivery device 136 sits within the guide mechanism 154 of the locator 116 and the device 100 is secured to the delivery device 136 via a suture or braided wire 136.

Figure 6:
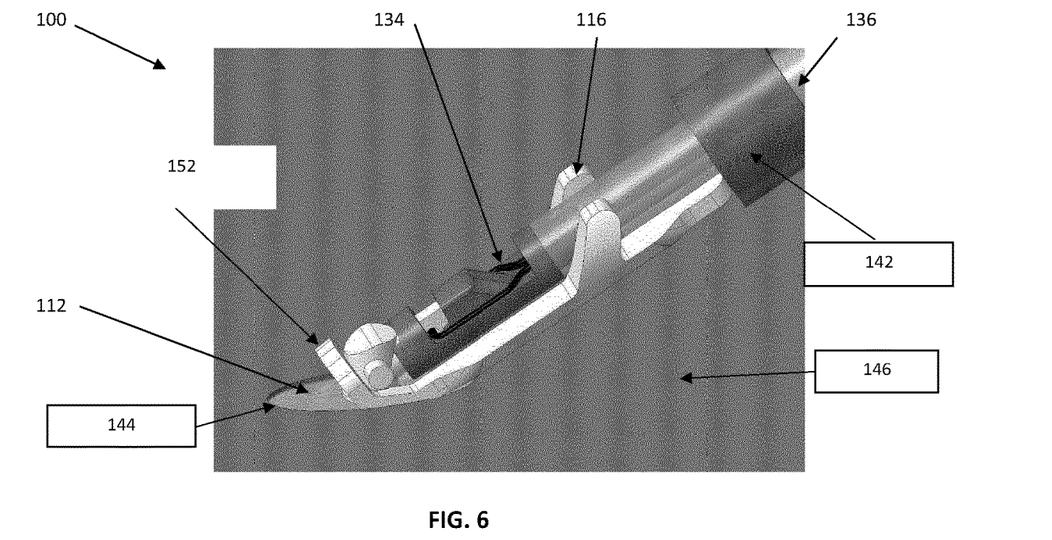
FIG. 6 is a perspective view of the device of FIG. 5 depicted in one stage of deployment in accordance with one or more embodiments of the invention.
Figure 7:
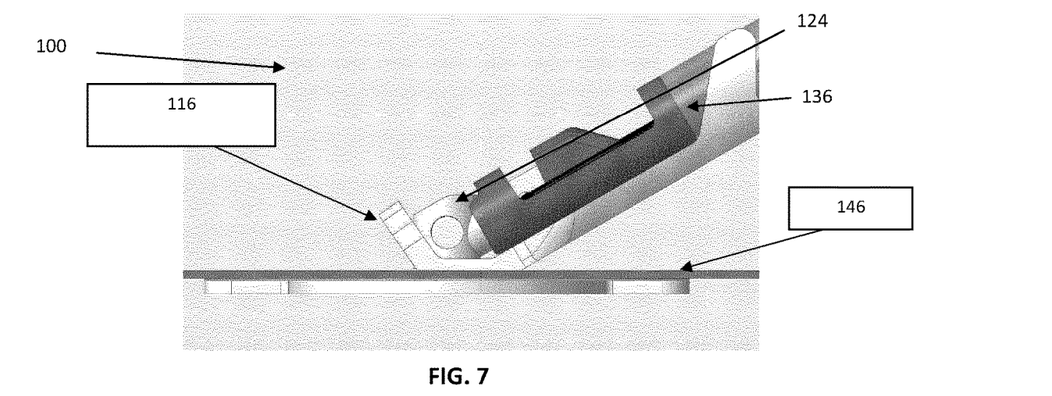
FIG. 7 is a side view of the device of FIG. 6 in accordance with one or more embodiments of the invention.

FIGS. 6 and 7 depict the device 100 positioned within the vessel, adjacent to the aperture 144 to be closed. As can be seen, a front edge (e.g., the non-planar distal end 152 of the locator) is positioned just above and outside of the aperture 144. As discussed below, this configuration allows the sealable member 112 and support member 114 to be inserted within the vessel, without the locator 116 engaging the vessel wall 146 prior to deployment. Also shown, is a push tube 142 disposed on the delivery device 136 for actuating the locator 116 from a first position to a second position. At this stage, the assembled device 110 has been pulled back so as to bring the sealable member 112 into contact with the vessel wall.

Figure 8:
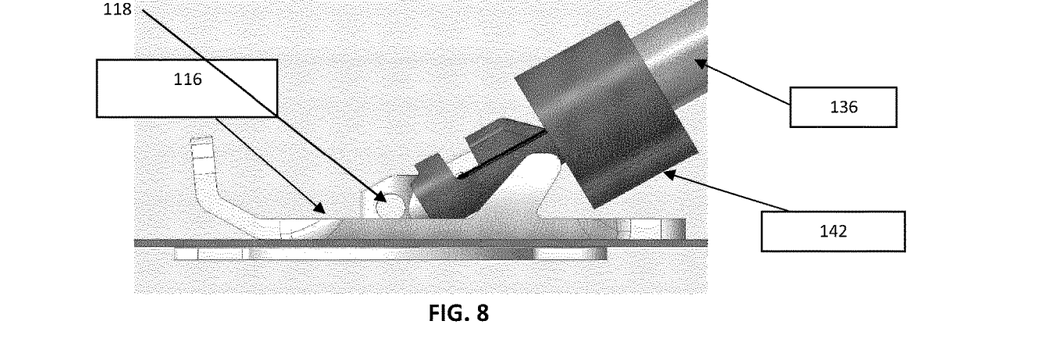
FIG. 8 is a side view of the device of FIG. 6 depicted in a later stage of deployment in accordance with one or more embodiments of the invention.

FIG. 8 depicts the device 100 after the locator 116 has been actuated to the second position outside of the vessel. As can be seen, the push tube 142 was advanced forward to engage the locator 116, pivoting it around the support shaft 118 into a flat or substantially planar orientation where the vessel wall 146 is secured between the locator 116 and the sealable member 112. The locator 116, and by extension the entire device 100 can be secured in place with any of the adjustment mechanism described below with respect to FIGS. 9-17.

Figure 9:
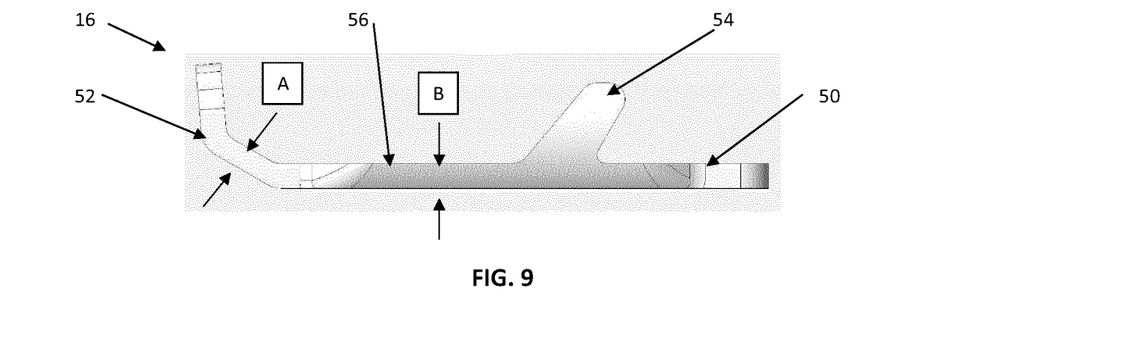
FIG. 9 is a cross-sectional view of a locator for use with a device in accordance with one or more embodiments of the invention.

FIGS. 9-17 depict various embodiments of locators for use with a device 10, 100 in accordance with one or more embodiments of the invention. Generally, the design intent of the locator 16, 116 is for it to be deployed upon the positioning the device 10, 100 at the puncture site. The basic locator is shown in FIG. 9 and includes an elongate body 50 that is substantially planar, a non-planar distal end 52 disposed at the front of the locator 16, and a guide mechanism 54 that extends upwardly from a top surface 60 of the locator to movably (e.g., slidably) engage the delivery tool. Generally, the front of the locator has an angled face that protrudes out of the vessel puncture site when the sealable member is in contact with the vessel wall. As discussed above, this non-planar portion can include any combination of angled and/or arcuate shapes as necessary to suit a particular application. The purpose of this non-planar face is to ensure that the locator 16 passes over the vessel wall during deployment and is not deployed inside the wall. The locator 16 is designed to have some flexibility so it can flex and bend to allow it to pass over the vessel wall without deforming or causing damage to the vessel tissue during the deployment.

Figure 10:
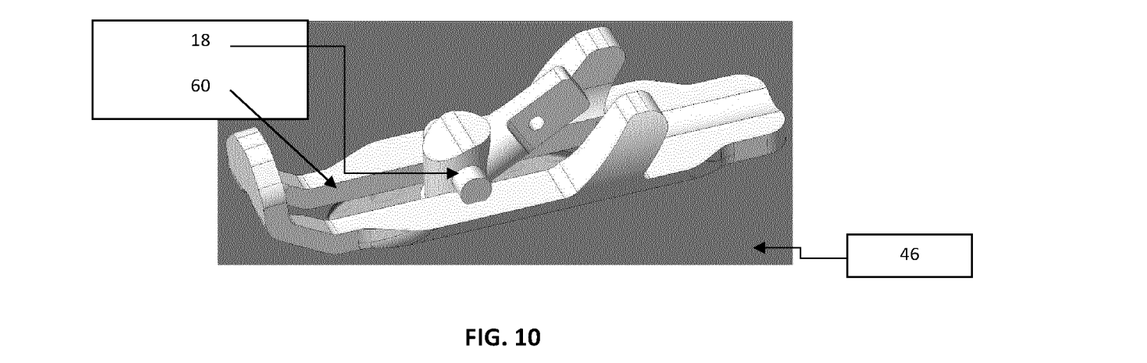
FIG. 10 is a perspective view of an alternative locator for use with a device in accordance with one or more embodiments of the invention.

At least a portion (e.g., A in FIG. 9) of the locator distal end 152 has a narrower cross-section than the main portion (e.g., B in FIG. 9) of the elongate body 50. This narrower area provides clearance for the locator 16 to be deployed between the support shaft 18 and the support member 14. This clearance is to allow the locator to bend and flex as it advances over the vessel wall. FIG. 10 depicts the locator 16 engaged with the support shaft 18 and in a deployed position. Generally, the device achieves closure by positioning the sealable member 12 against the vessel wall between the locator 16 and support member 14. The locator 16 is held in place by the support shaft 18 and its positioning relative to the vessel wall and the cross-sectional area at location B as shown in FIGS. 9 and 10.

Various alterations can be made to the locator 16 design (e.g., adding ramp or spring-like features) to allow the device 10 to close apertures in vessel walls of various thickness and topography. These alterations increase the range of wall thickness that the device may be used to close in the vessel wall.

Figure 11:
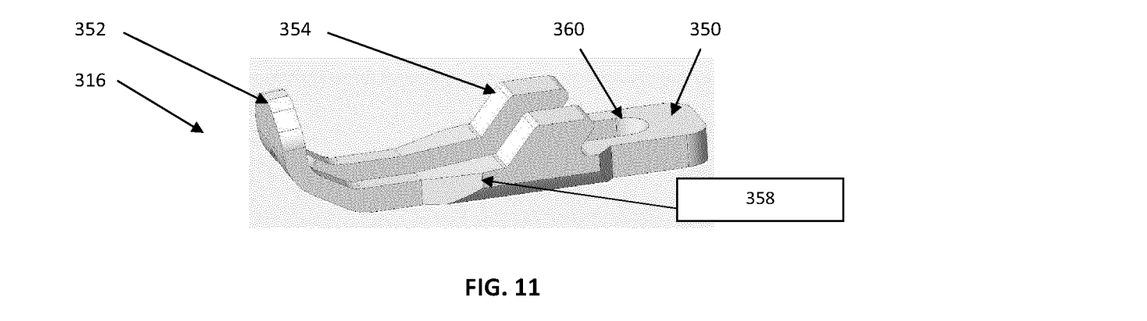
FIG. 11 is a perspective view of another alternative locator for use with a device in accordance with one or more embodiments of the invention.
Figure 12:
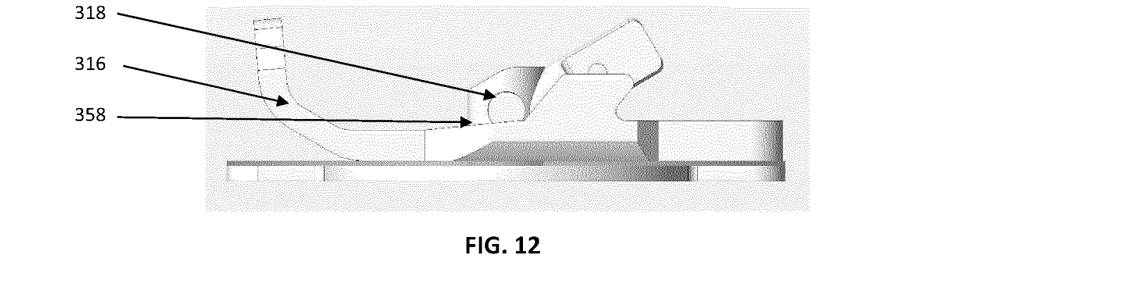
FIG. 12 is a side view of another alternative locator for use with a device in accordance with one or more embodiments of the invention.

FIGS. 11 and 12 depict a locator 316 where a portion of the top surface 360 has a ramped profile (e.g., adjustment mechanism 358) to increase the interference fit with the support shaft 318. FIG. 11 depicts the locator 316 alone, while FIG. 12 depicts the locator 316 engaging the support shaft 318.

Figure 13:
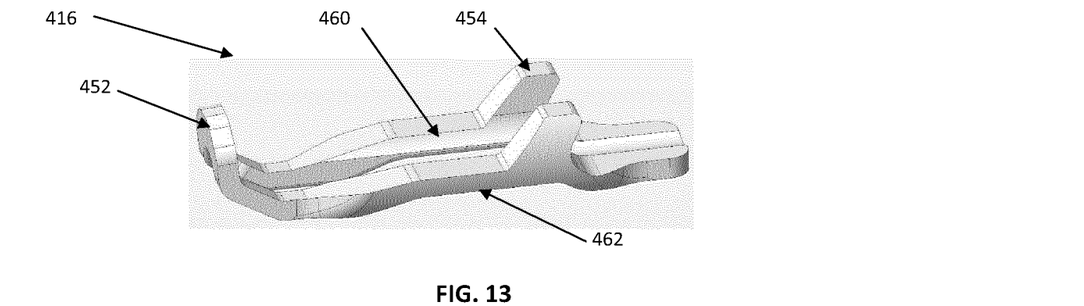
FIG. 13 is a perspective view of another alternative locator for use with a device in accordance with one or more embodiments of the invention.
Figure 14:
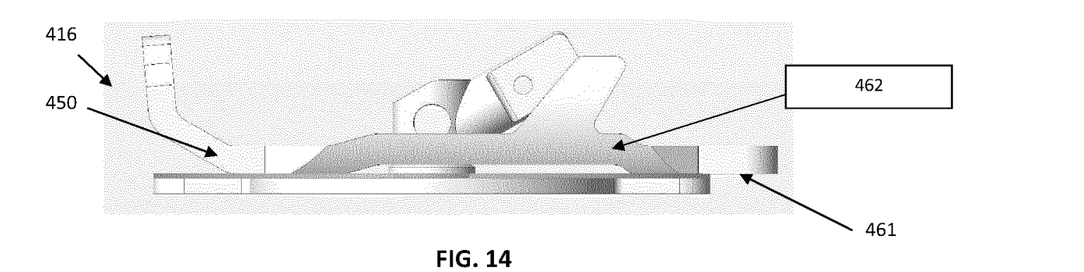
FIG. 14 is a side view of the alternative locator of FIG. 13 engaging with a support member in accordance with one or more embodiments of the invention.
Figure 15:
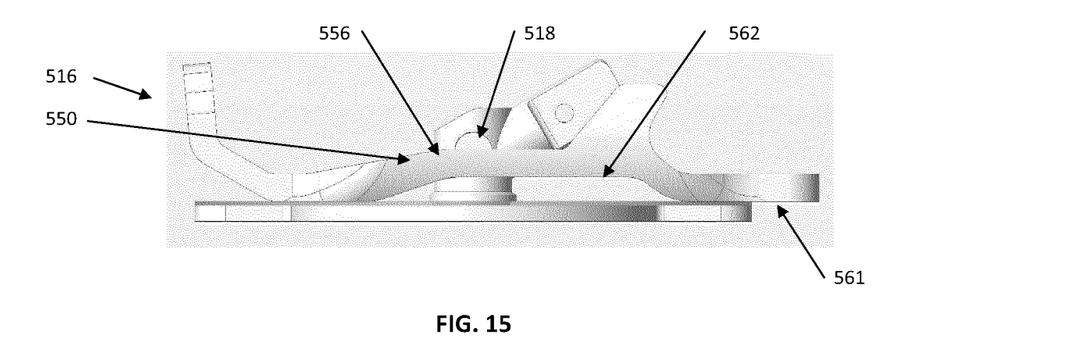
FIG. 15 is a side view of an alternative embodiment of the locator of FIG. 13 engaging with a support member in accordance with one or more embodiments of the invention.

FIGS. 13-15 depict a locator 416, 516 where a portion of the elongate body 450, 550 is non-planar. As shown in the figures, the portion of the elongate body that engages with the support shaft 418, 518 has an arcuate or angled portion (adjustment mechanism 462, 562) that defines a space between a bottom surface 461, 561 of the elongate body and an outer surface of the vessel wall. FIG. 13 depicts the locator 416 alone, while FIG. 14 depicts the locator 416 with a first profile and FIG. 15 depicts the locator 516 with a second, larger profile. These profiles can include any combination of arcuate and/or angled portions as necessary to suit a particular application and provide a spring force to the device. Specifically, the locator 416, 516 will act like a spring and pull the support member 414, 514 up into the vessel wall via the support shaft 418, 518, as can be seen in FIGS. 14 and 15. FIG. 15 depicts a locator 516 with a more exaggerated spring profile (adjustment mechanism 562) that can provide a greater force and/or be more suitable for vessels with very thin walls.

Figure 16:
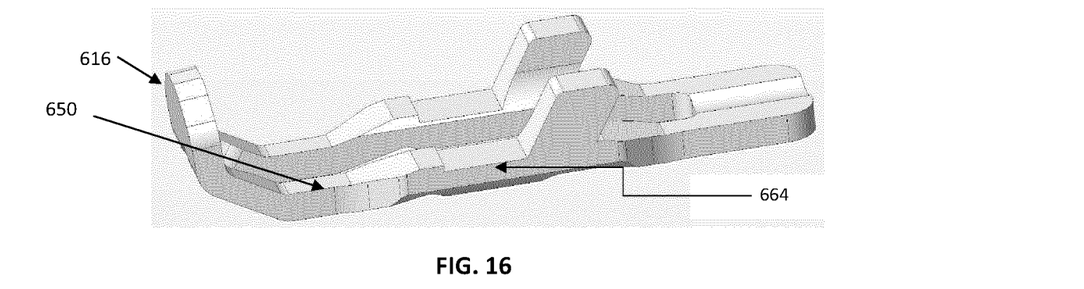
FIG. 16 is a perspective view of another alternative locator for use with a device in accordance with one or more embodiments of the invention.
Figure 17:
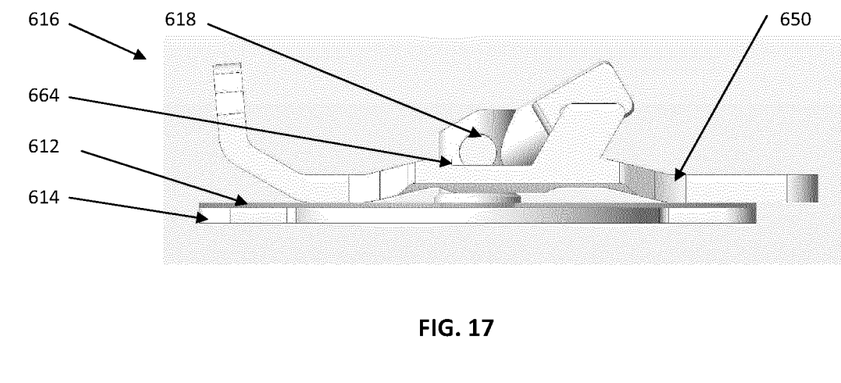
FIG. 17 is a side view of the alternative locator of FIG. 16 engaging with a support member in accordance with one or more embodiments of the invention.

FIGS. 16 and 17 depict a locator 616 where a portion of the elongate body 650 includes a cut-out (locator lock 664) in the top surface 660 of the elongate body 650. The lock 664 is located at a position on the elongate body 650 that substantially corresponds to where the locator 616 interfaces with the support shaft 618. The specific dimensions for the cut-out will vary to suit a particular application. FIG. 16 depicts the locator 616 alone, while FIG. 17 depicts the locator 616 engaged with the support shaft 618. The locator lock 664 can be used with any of the locator designs disclosed herein. As shown in FIG. 17, once deployed, the support shaft 618 is locked within the cut-out to prevent movement of the locator relative thereto.

FIGS. 18-20 and 22-24 depict various methods of using the device 700, 800 in accordance with one or more embodiments of the invention. Generally, the device 700, 800 is intended to close holes in hollow vessels having various sizes. It is particularly advantageous for closing blood vessels, such as arteries and veins, using a sealable member as disclosed here in conjunction with the locators and support members also disclosed herein. The design of the device is intended to provide the ability to be loaded into a loading cannula and delivered into a vessel in the same manner as the devices disclosed in the references incorporated hereinabove.

Figure 18A:
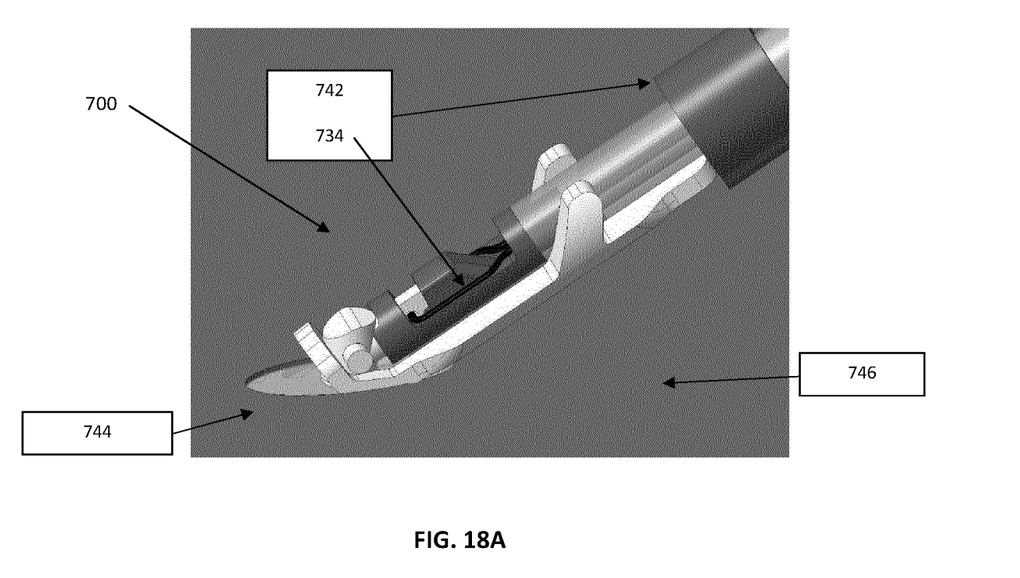
FIGS. 18A and 18B are perspective views of a device and delivery tool in various stages of deployment in accordance with one or more embodiments of the invention.
Figure 18B:
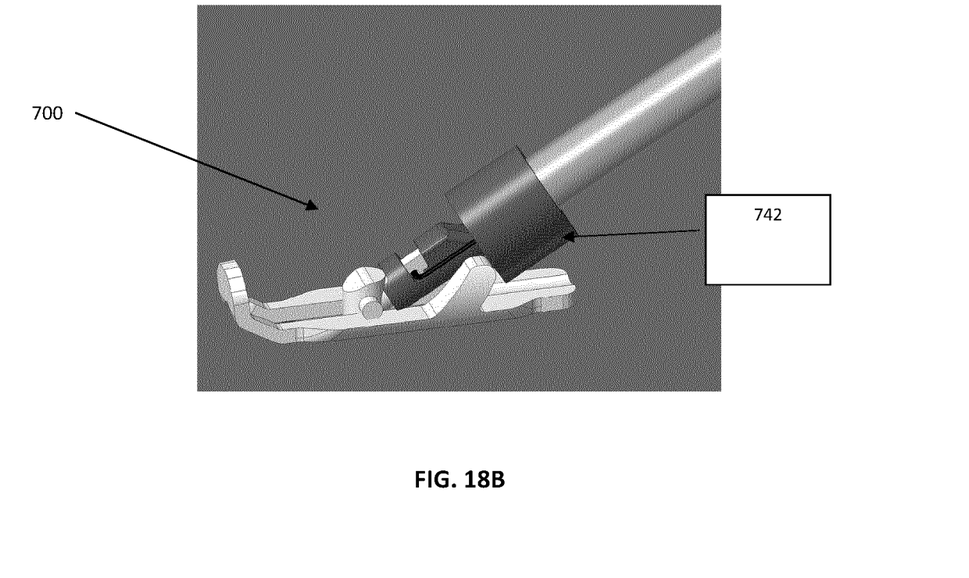
Figure 19A:
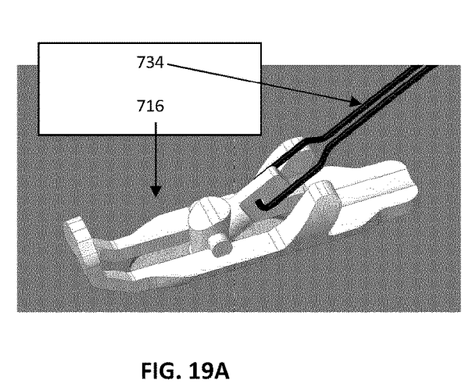
FIGS. 19A and 19B are perspective and side views of the device of FIGS. 18A and 18B after deployment in accordance with one or more embodiments of the invention.
Figure 19B:
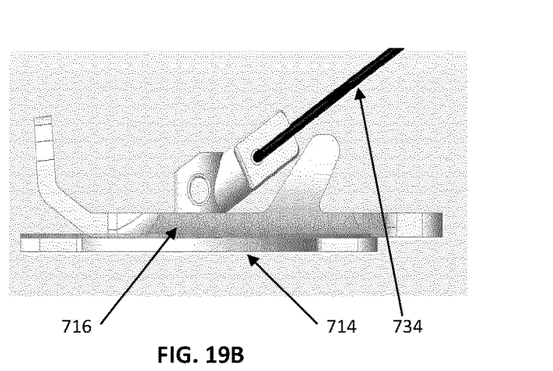
Figure 20A:
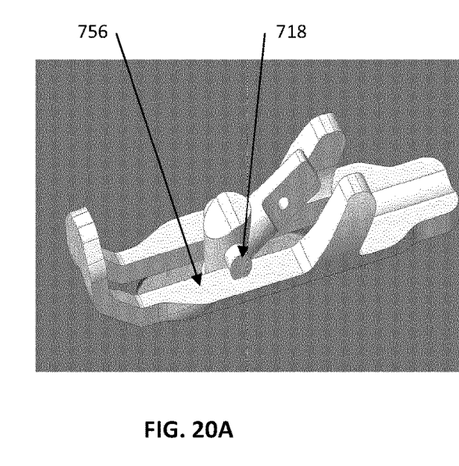
FIGS. 20A and 20B are perspective and side views of the device of FIGS. 19A and 19B in a later state of deployment in accordance with one or more embodiments of the invention.
Figure 20B:
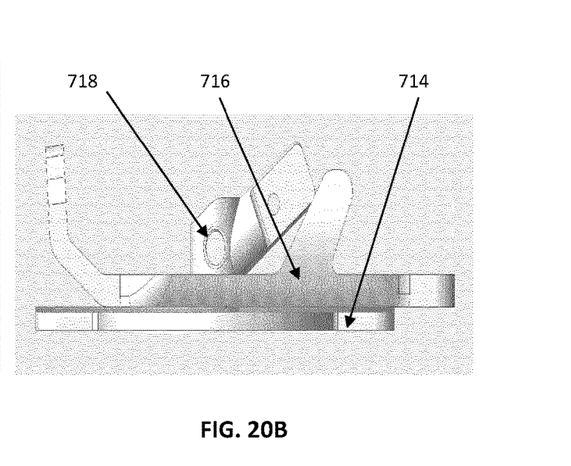

FIGS. 18-20 generally depict the deployment of the device as follows. After the sealable and support members have been positioned within the vessel, the device is pulled back to tamponade (e.g., provide a closure to the aperture in the vessel wall (FIG. 18A)). Once affective tamponade has been achieved, the locator 716 is deployed by advancing the push tube 742 forward (FIG. 18B). Once the locator 716 has been deployed the suture/braided wire 734 is released from the device handle and the handle is removed (FIGS. 19A and 19B). If hemostasis has been achieved the suture/braided wire 734 is removed, thereby completing the closure (FIGS. 20A and 20B). If the puncture site continues to bleed, a small amount of tension can be pulled on the suture until hemostasis is achieved.

Figure 22:
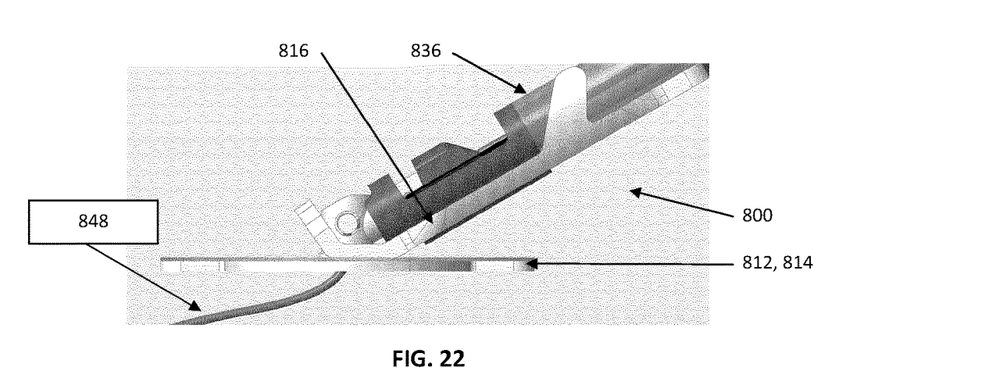
FIGS. 22-24 are perspective views of a device and delivery tool in various stages of deployment in accordance with one or more embodiments of the invention.
Figure 23:
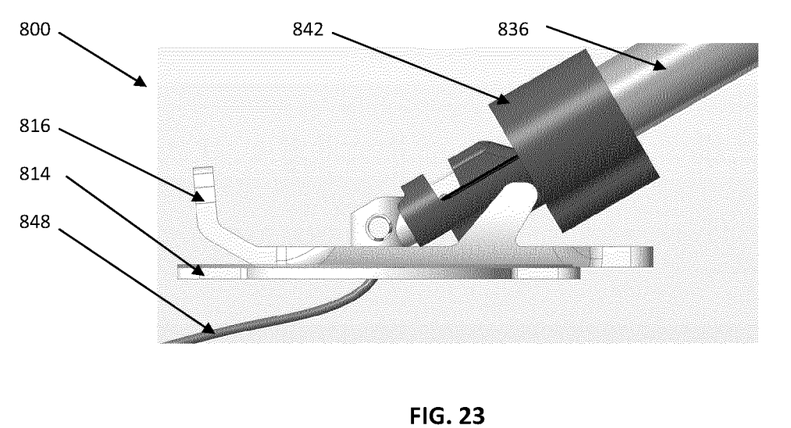
Figure 24:
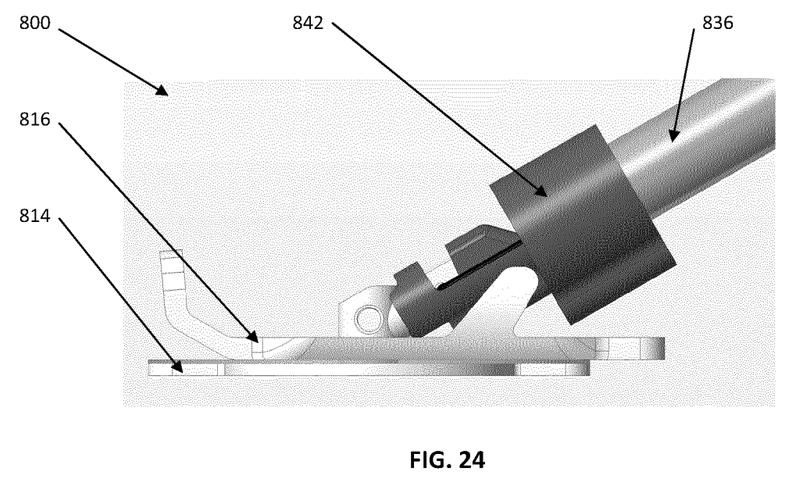

The device 800 is generally designed for the delivery over a guidewire via a catheter to the inside of a hollow vessel (FIGS. 22-24). The device 800 (e.g., the support member 814 and the sealable member 812) is first folded into a delivery system and then delivered over a guidewire 848 via an introducer 836 into the inside of the vessel. Once inside the vessel, the device is allowed to open into its original, pre-delivery shape (FIG. 22). The next step is to gently bring the device back to the aperture in the vessel over the guidewire 848 with the delivery system (FIG. 23). Once there, the device (e.g., support member 814) hooks the distal rim of the aperture and will then seal the aperture when located fully across the aperture. Thereafter, the guidewire 148 is removed and the locator 816 is moved to its final straddling position (FIG. 24). The device 800 is released from the delivery system and the delivery system is removed.

FIGS. 21A-21C depict the sealable member as discussed above. Generally, the sealable member 12 is made of a bilayer bioabsorbable polymer film consisting of an extruded component and an electrospun component that may be formed as two distinct layers that are joined together or as a single component. The extruded layer may range between about 10 μm-500 μm in thickness. The electrospun layer may consist of fibers in the range of about 0.3 μm-30 μm diameter, with a layer thickness in the range of about 10 μm-2000 μm. The fibers may be arranged in a random or patterned orientation and their diameter and density may vary within the electrospun layer. In one example, the electrospun layer next to the extruded layer consists of high density of narrow fibers, and as the depth of the electrospun layer increases, the fibers become larger in diameter and less dense (more porous), resulting in a softer top surface on the electrospun layer to facilitate conforming with the topography of the inner lumen of the vessel when pulled back into location to close the aperture.

An alternative sealable member 12 is entirely electrospun and consists of fibers in the range of about 0.1 μm-30 μm diameter and with a layer thickness in the range of about 50 μm-2500 μm. This alternative member 12 will have a bottom surface that is impermeable or semi-impermeable with a softer top surface on the electrospun layer to facilitate conforming to the topography of the inner lumen of the vessel when pulled back into location to close the hole.

Generally, the locator ensures that the aperture is sealed between the sealable member and the vessel surface regardless of the vessels surface topography (e.g., calcification, plaque, disease, valves in the case of veins, varying wall thicknesses, or dissections at the puncture site. The locator enables the device to be tailored to close a wide variety of vessels as the locator's geometry can be changed to accommodate a thick vessel wall (e.g., an aorta) or a thin vessel wall (e.g., a femoral vein or large intestine). The locator/device geometry and size can be adjusted to close large or small vascular openings. Additionally, the device can accommodate a procedural guidewire to facilitate an over the wire delivery to the vessel, such as a 0.038", 0.035", 0.018", or 0.014" diameter guide wire.

The locator can provide contact on both a distal side and a proximal side of the external vessel wall when the device is deployed. When combined with the support shaft, the locator 16 provides for a range of operation in adapting to different wall thicknesses in the vessels that have apertures for closing and can facilitate closing larger apertures (e.g., >24 F). When used in a venous vessel, for example, there is minimal recoil at a puncture site, as the locator design straddles both the distal and proximal sides of the aperture. The device also provides for a faster closure and improved sealing due to the snap-in effect of the locator on both the distal and proximal sides of the device, thereby providing better security and less risk of dislodgement due to the design of the locator gripping on both the distal and proximal sides of the aperture. Additionally, the device will better adapt to rough and uneven inner lumen surfaces of the vessel wall due to the novel support member design combined with the design of the locator. Such a robust deployment (e.g., more difficult to move/dislodge once deployed) minimizes the risk of embolization. The device may be used in transcaval, patent foramen ovale (PFO), or natural orifice transluminal endoscopic surgery (NOTES) closures. The device also provides a direct means to control the apposition of the device at the aperture, thereby better managing any bleeding post deployment.

Although certain figures and embodiments relate to use of systems and devices for closure of a perforation associated with vascular surgery, one of ordinary skill in the art will appreciate that components of a provided device are not size dependent (e.g., are scalable) and are therefore useful for closure of any perforation in a lumen of a mammal.

Additionally, it is contemplated that systems, devices, methods, and processes of the present application encompass variations and adaptations developed using information from the embodiments described in the following description. Adaptation or modification of the methods and processes described in this specification may be performed by those of ordinary skill in the relevant art.

Throughout the description, where compositions, compounds, or products are described as having, including, or comprising specific components, or where processes and methods are described as having, including, or comprising specific steps, it is contemplated that, additionally, there are articles, devices, and systems of the present application that consist essentially of, or consist of, the recited components, and that there are processes and methods according to the present application that consist essentially of, or consist of, the recited processing steps.

It should be understood that the order of steps or order for performing certain action is immaterial so long as the described method remains operable. Moreover, two or more steps or actions may be conducted simultaneously.

What is claimed:

1. A device for sealing an aperture in a tissue of a body lumen, the device comprising:
    a sealable member positionable against an interior surface of the tissue adjacent the aperture in the tissue when the device is in a sealing position;
    a support member comprising a base and a column, wherein the base of the support member comprises a support surface to support the sealable member against the interior surface of the tissue when the device is in the sealing position and the column extends through the sealing member and the aperture and comprises an engagement mechanism; and
    a locator pivotably coupled to the support member via the engagement mechanism and positionable against an exterior surface of the tissue adjacent the aperture when the device is in the sealing position, so that at least a portion of the tissue is disposed between the locator and the sealable member, wherein the locator comprises an adjustment mechanism for accommodating varying tissue topographies, wherein the locator comprises a proximal portion disposed on a proximal side of the aperture and a distal portion disposed on a distal side of the aperture,
    wherein the engagement mechanism comprises:
        a portion of the column disposed transversely to the support surface and defining an aperture therein; and
        a support shaft configured to be disposed within the column aperture to secure the locator to the support member,
    wherein the support shaft engages with a surface of the locator to provide a sealing force to the tissue; and
    wherein the adjustment mechanism comprises at least one of:
        a section of the elongate body comprising a length of varying thickness to create a ramp for slidably engaging the engagement mechanism; or
        a section of the elongate body comprising a non-planar portion configured to flex when engaged with the engagement mechanism.

2. The device of claim 1, wherein the locator comprises:
    an elongate, substantially planar body;
    a non-planar distal portion;
    a guide mechanism for engaging with a delivery device for deploying the locator; and
    the adjustment mechanism disposed along the elongate body,
    wherein the guide mechanism comprises two rails disposed at the exterior sides of and extending upward from a top surface of the elongate body, wherein the rails define a space therebetween for slidably engaging the delivery device.

3. The device of claim 2, wherein the elongate body comprises a cut-out portion on a top surface thereof for locking the locator in place when engaged with the engagement mechanism.

4. The device of claim 2, wherein the locator is deployed via a push-tube located on the delivery device pushing against the guide mechanism.

5. The device of claim 2, wherein the elongate body defines a substantially centrally located, elongate opening configured for engaging with the engagement mechanism.

6. The device of claim 2, wherein the non-planar distal portion of the elongate body comprises at least one angular portion.

7. The device of claim 2, wherein the non-planar distal portion comprises a first angular portion extending upwardly from the elongate body and a second angular portion extending from the first angular portion.

8. The device of claim 2, wherein the non-planar distal portion of the elongate body comprises at least one arcuate portion.

9. The device of claim 1, wherein the column of the base of the support member comprises a shoulder portion to secure the sealable member to the support member via crimping.

10. The device of claim 1, wherein the sealable member and the support member, collectively, form a single integrated structure via a non-fixed mating.

11. The device of claim 1, wherein the device is configured to be deployed over a guidewire.

12. The device of claim 1, wherein the column of the support member comprises:
 a substantially cylindrical base portion disposed transversely to the support surface; and
 a neck portion extending angularly from a top portion of the base portion and defining an aperture along an axis corresponding to a longitudinal axis of a delivery shaft to which the support member is releasably attached.

13. The device of claim 1, wherein the column further comprises a shoulder configured for at least one of aligning or securing the sealable member.

14. The device of claim 1, wherein the base of the support member comprises:
 a substantially circular scaffolding comprising one or more rings; and
 an elongate, central spine comprising a proximal end and a distal end, wherein the spine extends through a center point of the circular scaffolding and each of the proximal and distal ends extend beyond an outer diameter of the scaffolding.

15. The device of claim 14, wherein the central spine is substantially rigid, and at least one end thereof is configured to engage with the aperture in the tissue.

16. A closure system for sealing an aperture in a tissue of a body lumen, the system comprising:
 a delivery device; and
 a closure device comprising:
  a sealable member positionable against an interior surface of the tissue adjacent the aperture in the tissue when the device is in a sealing position;
  a support member comprising a base and a column, wherein the base of the support member comprises a support surface to support the sealable member against the interior surface of the tissue when the device is in the sealing position and the column extends through the sealing member and the aperture and comprises an engagement mechanism; and
  a locator pivotably coupled to the support member via the engagement mechanism and positionable against an exterior surface of the tissue adjacent the aperture when the device is in the sealing position, so that at least a portion of the tissue is disposed between the locator and the sealable member, wherein the locator comprises an adjustment mechanism for accommodating varying tissue topographies, wherein the locator comprises a proximal portion disposed on a proximal side of the aperture and a distal portion disposed on a distal side of the aperture,
 wherein the delivery device has an attachment mechanism to releasably attach the closure device for delivery to the aperture in the tissue and is configured to deploy the closure device within the lumen,
 wherein the engagement mechanism comprises:
  a portion of the column disposed transversely to the support surface and defining an aperture therein; and
  a support shaft configured to be disposed within the column aperture to secure the locator to the support member, wherein the support shaft engages with a surface of the locator to provide a sealing force to the tissue,
 wherein the adjustment mechanism comprises at least one of:
  a section of the elongate body comprising a length of varying thickness to create a ramp for slidably engaging the engagement mechanism; and
  a section of the elongate body comprising a non-planar portion configured to flex when engaged with the engagement mechanism, and
 wherein the attachment mechanism comprises a suture or a braided wire.

17. A method of securing a device for sealing an aperture in a tissue of a body lumen, the method comprising the steps of:
 positioning at least a portion of the device within the body lumen via a delivery device;
 deploying a sealable member against an interior surface of the tissue adjacent the aperture in the tissue;
 deploying a support member comprising a base and a column, wherein the base of the support member comprises a support surface to support the sealable member against the interior surface of the tissue when the device is in the sealing position and the column extends through the sealing member and the aperture and comprises an engagement mechanism; and
 actuating a locator pivotably coupled to the support member via the engagement mechanism from a first position to a second position to engage a wall of the body lumen and secure the device in place,
 wherein the locator comprises a proximal portion disposed on a proximal side of the aperture and a distal portion disposed on a distal side of the aperture, and
 wherein the support shaft engages with a surface of the locator to provide a sealing force to the tissue.

18. The method of claim 17 further comprising the step of:
 positioning the locator relative to the column of the support member so that an adjustment mechanism on the locator engages at least a portion of the column to accommodate a lumen wall with an irregular topography.

\* \* \* \* \*